(12) United States Patent
Basiri et al.

(10) Patent No.: US 11,529,531 B2
(45) Date of Patent: Dec. 20, 2022

(54) USING REINFORCEMENT LEARNING IN RADIATION TREATMENT PLANNING OPTIMIZATION TO LOCATE DOSE-VOLUME OBJECTIVES

(71) Applicant: SIEMENS HEALTHINEERS INTERNATIONAL AG, Palo Alto, CA (US)

(72) Inventors: Shahab Basiri, Siuntio (FI); Esa Kuusela, Espoo (FI); Elena Czeizler, Helsinki (FI); Mikko Oskari Hakala, Rajamäki (FI)

(73) Assignee: SIEMENS HEALTHINEERS INTERNATIONAL AG

( * ) Notice: Subject to any disclaimer, the term of this patent is extended or adjusted under 35 U.S.C. 154(b) by 0 days.

(21) Appl. No.: 16/896,237

(22) Filed: Jun. 9, 2020

(65) Prior Publication Data
US 2021/0379404 A1 Dec. 9, 2021

(51) Int. Cl.
*A61N 5/10* (2006.01)
(52) U.S. Cl.
CPC ......... *A61N 5/1031* (2013.01); *A61N 5/1038* (2013.01)
(58) Field of Classification Search
None
See application file for complete search history.

(56) References Cited

U.S. PATENT DOCUMENTS

| | | | |
|---|---|---|---|
| 9,731,147 | B2 | 8/2017 | Nord et al. |
| 2013/0204067 | A1* | 8/2013 | Nord ............. A61N 5/1038 600/1 |
| 2019/0083813 | A1 | 3/2019 | Ruokokoski et al. |
| 2020/0206534 | A1* | 7/2020 | Bzdusek ......... A61N 5/1039 |

FOREIGN PATENT DOCUMENTS

WO 2016088075 A1 6/2016

OTHER PUBLICATIONS

International Search Report and Written Opinion of the International Searching Authority, International application No. PCT/EP2021/065110, dated Sep. 20, 2021.

* cited by examiner

*Primary Examiner* — Hoon K Song
(74) *Attorney, Agent, or Firm* — Su IP Consulting

(57) ABSTRACT

A reinforcement learning agent facilitates optimization of a radiation-delivery treatment plan. The reinforcement learning agent is configured to generate a radiation-delivery treatment plan that can exceed the quality of a plan or plans employed to train the reinforcement learning agent. The reinforcement learning agent is trained to evaluate a radiation-delivery treatment plan that is output by an optimization software application, modify one or more dose-volume objective parameters of the evaluated radiation-delivery treatment plan, and then input the modified radiation-delivery treatment plan to the optimization software application for further optimization. The reinforcement learning agent adaptively adjusts the one or more dose-volume objective parameters based on an action policy learned during a reinforcement learning training process.

20 Claims, 10 Drawing Sheets

USING REINFORCEMENT LEARNING IN RADIATION TREATMENT PLANNING OPTIMIZATION TO LOCATE DOSE-VOLUME OBJECTIVES

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on a planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated, a planning target volume can be determined, and an appropriate treatment plan can be generated. When implemented, such a treatment plan results in certain predetermined treatment objectives being met, such as the planning target volume receiving a radiation dose that exceeds a minimum required threshold value, surrounding tissue receiving a radiation dose that does not exceed a maximum allowable threshold value, homogeneity of the radiation dose to the planning target volume meeting a minimum threshold value, and the like.

Due to the geometric complexities in applying a radiation treatment to a three-dimensional target that can be in close proximity to one or more organs at risk (OARs), treatment planning is a complex process that can involve the participation of multiple highly trained medical professionals and analysis using sophisticated software. As a result, generation of a treatment plan that correctly doses a planning target volume without excessively dosing nearby OARs is a multi-step process, where each step can be time-consuming and often can only be performed by expert personnel. In intensity-modulated radiation therapy (IMRT), in which photon and/or proton beams are conformed to the shape of a tumor, one such planning step is IMRT optimization.

In IMRT optimization, one or more treatment plans are optimized for the treatment of a particular patient. That is, one or more beam geometries for implementing the planned treatment are determined and a dose distribution for each beam geometry is optimized. In some instances, a qualified dosimetrist employing a software application, sometimes referred to as an "optimizer," determines the one or more beam geometries and optimizes the associated dose distribution, then a physician responsible for the patient typically approves one or more of the treatment plans. In some instances, the software application may generate one or more beam geometries and associated optimized dose distributions during IMRT optimization, and a dosimetrist may select, modify, and/or review the output of the software application.

One drawback to conventional IMRT optimization is that scoring the tradeoffs between target coverage and OAR sparing heavily depends on the location of dose-volume histogram objectives. For a specific patient, such objective locations are not known before planning. Typically, an IMRT planner or dosimetrist starts with some initial guess and proceeds with repeatedly adjusting the objective locations for a planning target volume through several rounds of optimization until the treatment plan becomes clinically acceptable. For example, in such a treatment plan, a minimum dosage is applied to the planning target volume while a maximum dosage that can be tolerated by a particular OAR of the patient is not exceeded. Thus, the IMRT planner oversees optimization of various IMRT treatment plans until one or more treatment plans are generated that meet the clinical goals established for the specific patient. This implies that not only is generating a treatment plan time-consuming, the quality of the plan may vary among IMRT planners depending on the level of experience of the IMRT planner, clinical feedback available to the IMRT planner, and the time available to the IMRT planner to optimize a specific plan.

Another drawback to conventional IMRT optimization is that the quality of a particular optimized treatment plan is strongly dependent on the multiple conflicting dose-volume objectives associated with a particular planning target volume. For example, there is generally a trade-off between how high the dose applied to the planning target volume can be and how low the resultant dose received by an OAR can be. In another example, a relaxation of the homogeneity of dose in a planning target volume may enable lower dose in an OAR. Consequently, the threshold values for such dose-volume objectives are often modified by the IMRT planner to generate a higher quality-treatment plan. However, balancing such competing dose-volume objectives is generally considered to be an intuitive undertaking, and as a result, IMRT optimization does not include a rigorous exploration of the many possible treatment plans that can be optimized based on the many possible permutations of dose-volume objectives that can be considered for a particular planning target volume.

SUMMARY

In accordance with at least some embodiments of the present disclosure, a reinforcement learning (RL) agent facilitates optimization of a radiation-delivery treatment plan. Specifically, the RL agent is configured to generate a radiation-delivery treatment plan that can exceed the quality of a plan or plans employed to train the RL agent. The RL agent is trained to evaluate a radiation-delivery treatment plan that is output by an optimization software application, modify one or more dose-volume objective parameters of the evaluated radiation-delivery treatment plan, and then input the modified radiation-delivery treatment plan to the optimization software application for further optimization. The RL agent adaptively adjusts the one or more dose-volume objective parameters based on an action policy learned during a reinforcement learning training process. In the training process, the RL agent develops the action policy for adjusting one or more dose-volume objective parameters so that a reward is maximized or otherwise increased. The reward can be defined in terms of multiple dose-volume objectives and/or other treatment goals, such as target coverage, sparing of organs at risk, homogeneity of dose applied to the planning target volume, and conformity of the region receiving a prescribed dose to the planning target volume (conformity index), among others.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
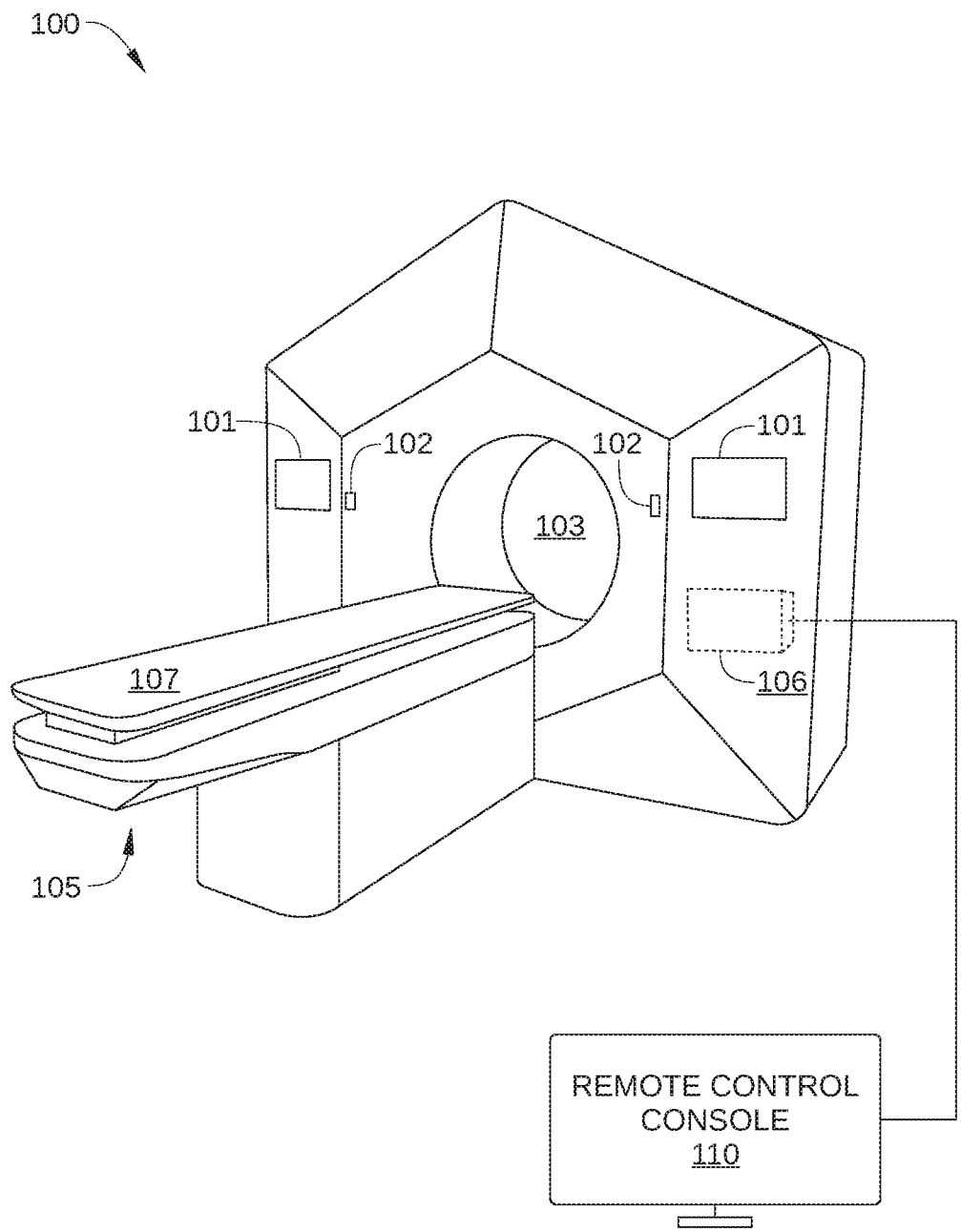
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. For example, in some embodiments, RT system 100 is configured to perform intensity-modulated radiation therapy (IMRT). As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection.

Generally, RT system 100 is capable of kV imaging of a target volume during application of an MV treatment beam, so that an image-guided radiation therapy (IGRT) process can be performed using X-ray imaging. Alternatively, in some embodiments, RT system 100 is configured to perform an IMRT process without IGRT. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as buttons and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
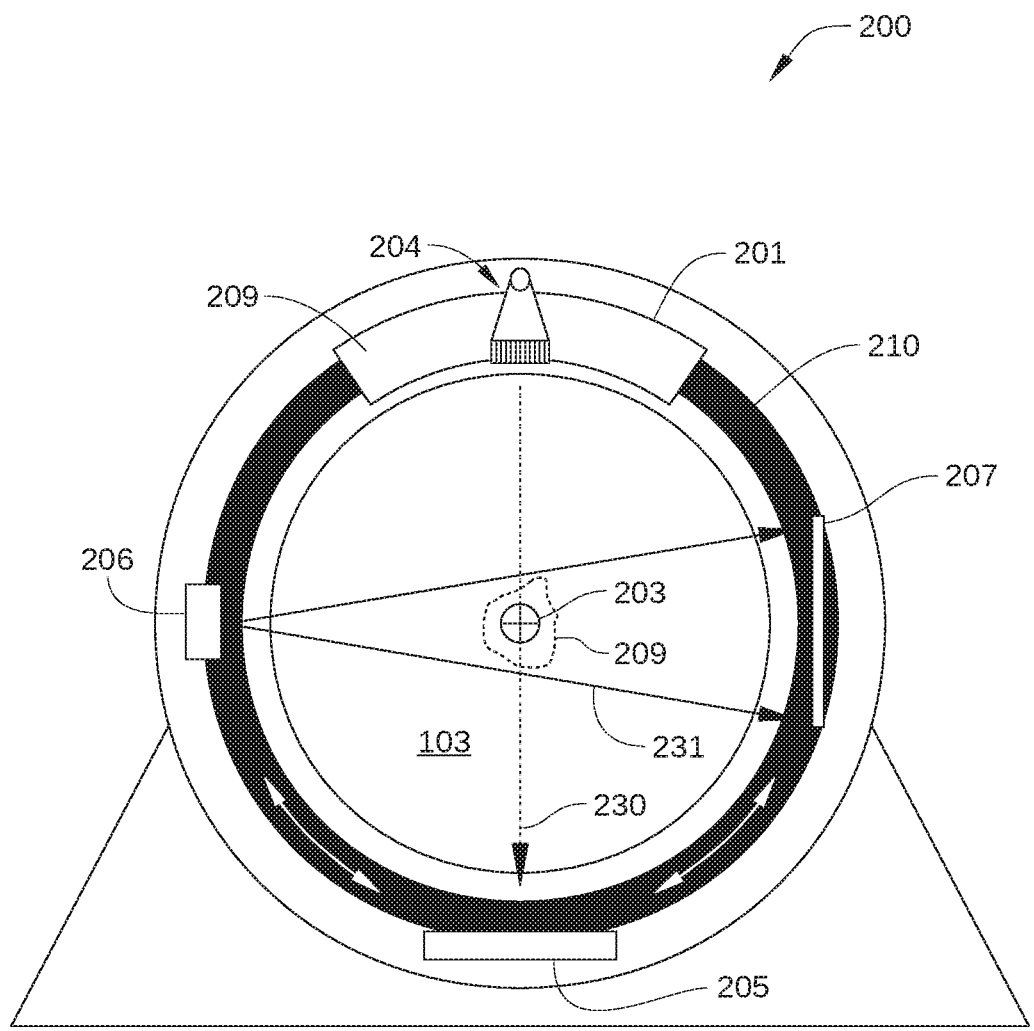
FIG. 2 schematically illustrates a drive stand and a gantry of the RT system in FIG. 1, according to various embodiments of the current disclosure.

FIG. 2 schematically illustrates a drive stand 200 and gantry 210 of RT system 100, according to various embodiments of the current disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 210 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In the embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively or additionally, in some embodiments, partial-data reconstruction may be performed by RT system 100 during portions of an IGRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Alternatively, CBCT may be employed during portions of an IGRT process to generate a 3D reconstruction of target volume 209 during treatment.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. Thus, in such embodiments, RT system 100 includes a first imaging X-ray source and a corresponding X-ray imager mounted on gantry 210 and a second imaging X-ray source and corresponding X-ray imager mounted on gantry 210.

The projection images generated by X-ray imager 207 are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 3.

Figure 3:
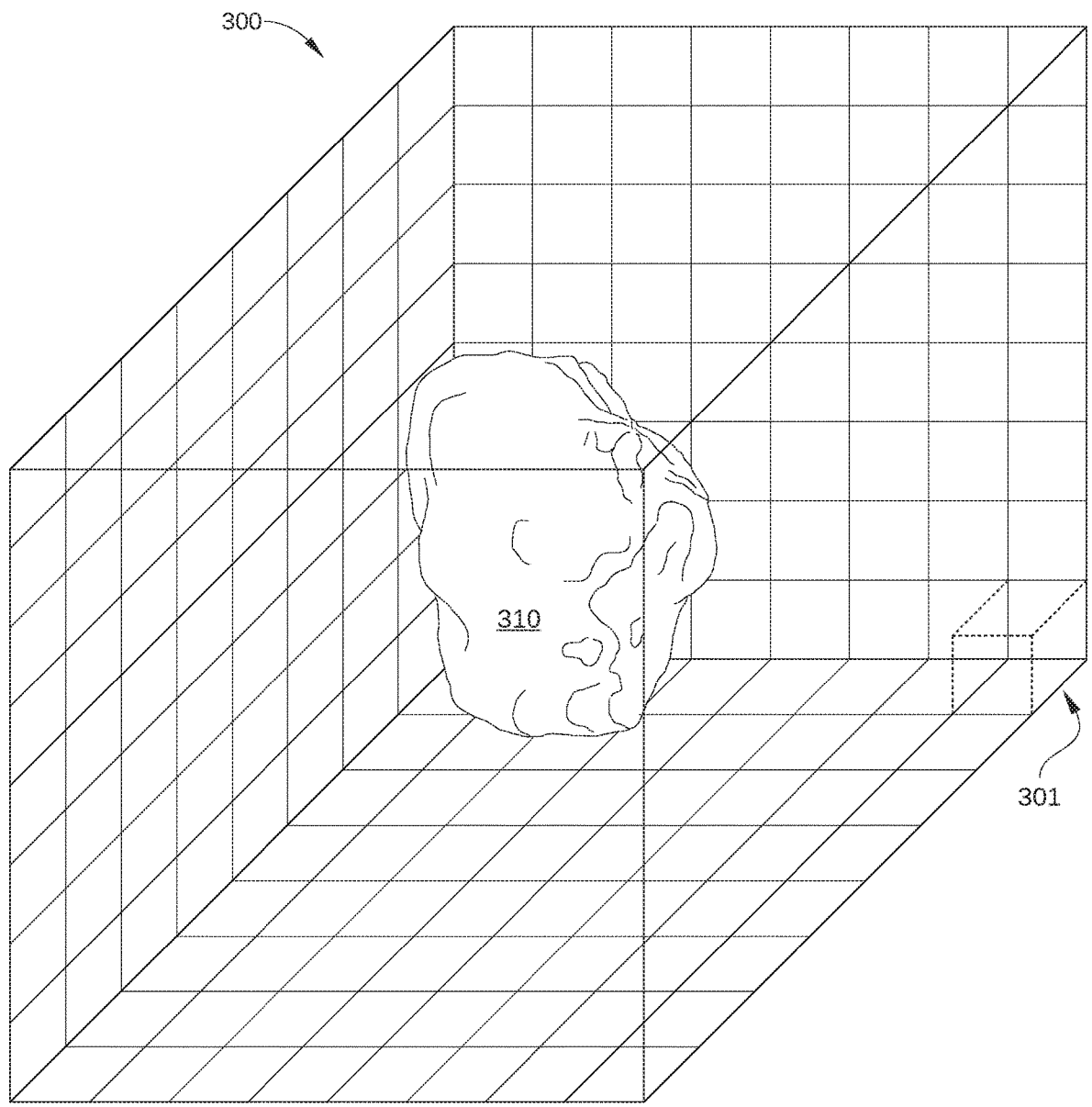
FIG. 3 schematically illustrates a digital volume that is constructed based on projection images that show a tumor and a region of anatomy around the tumor.

FIG. 3 schematically illustrates a digital volume 300 that is constructed based on projection images that show a tumor and a region of anatomy around the tumor. For example, digital volume 300 may be constructed based on one or more treatment planning computed tomography (CT) scans performed by an X-ray imager. The X-ray imager can be an imaging device separate from RT system 100 or can be an X-ray imager included in RT system 100.

Digital volume 300 includes a plurality of voxels 301 (dashed lines) of anatomical image data, where each voxel 301 corresponds to a different location within digital volume 300. For clarity, only a single voxel 301 is shown in FIG. 3. Digital volume 300 corresponds to a 3D region that includes target volume 310. In FIG. 3, digital volume 300 is depicted as an 8×8×8 voxel cube, but in practice, digital volume 300 generally includes many more voxels, for example orders of magnitude more than are shown in FIG. 3.

For purposes of discussion, target volume 310 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk (OARs). Thus, the PTV is generally larger than the CTV, but in some situations can also be reduced in some portions to provide a safety margin around an OAR. The PTV is typically determined based on imaging performed prior to the time of treatment.

Figure 4:
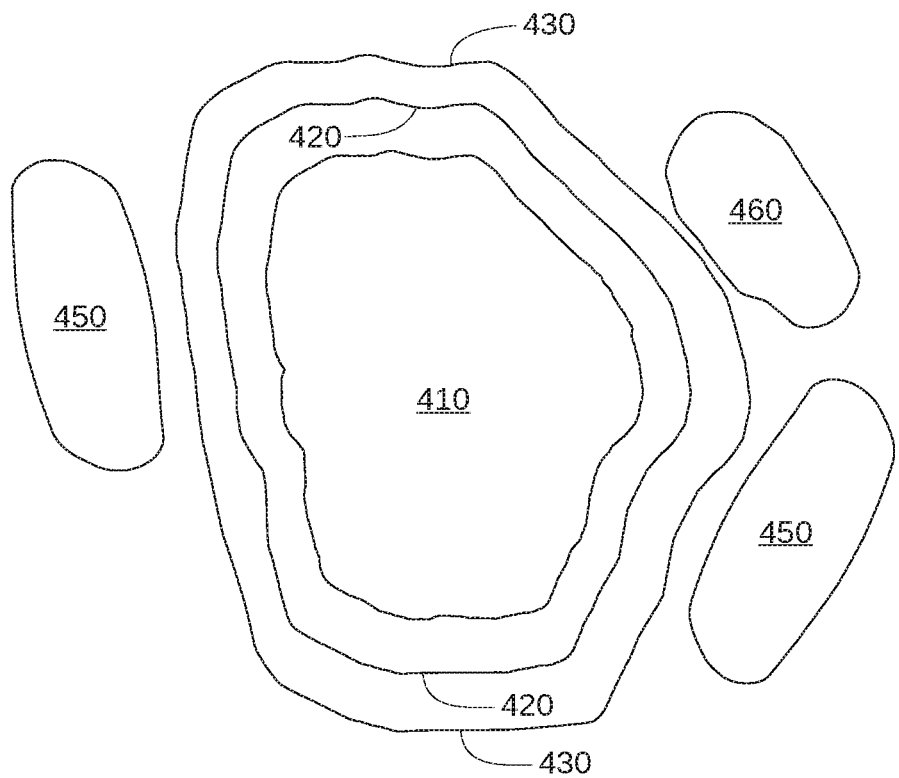
FIG. 4 schematically illustrates examples of a gross tumor volume, a clinical target volume, a planning target volume, two organs at risk, and a critical structure.

FIG. 4 schematically illustrates examples of a GTV 410, a CTV 420, a PTV 430, two OARs 450, and a critical structure 460. It is noted that the structures included in FIG. 4 are depicted in two dimensions, but are generally three-dimensional in nature. As such, GTV 410, CTV 420, PTV 430, OARs 450, and critical structure 460 are each typically defined via a three-dimensional segmentation process, in which a region of specific voxels (not shown in FIG. 4) that are included in a set of treatment planning CT scans is indicated as a particular structure. GTV 410, CTV 420, and PTV 430 are regions or structures that an ideal treatment plan causes to receive at least a minimum threshold dose, while OARs 450 and critical structure 460 are regions or structures of normal tissue that an ideal treatment plan causes to receive as little dose as possible.

Generally, a treatment planning directive for a particular patient is generated based on a treatment planning CT, such as digital volume 300 of FIG. 3, that includes the GTV, CTV, and/or PTV for that patient. The treatment planning directive typically describes image studies for a treatment site, including target tissue structures and normal tissue structures to be defined via the imaging studies. These target and normal tissue structures are subsequently used for treatment planning. For scoring multiple treatment plans within an optimization process, the treatment planning directive may also specify expansions of the target tissue structures and normal tissue structures. Thus, in addition to the GTV, the treatment planning directive may further include a CTV, the internal target volume (ITV), a PTV, OARs, critical structures, and/or a planning OAR volume (PRV), among others. The treatment planning directive may further specify radiation therapy prescription guidelines, planning suggestions, and/or special instructions.

Treatment Plan Optimization Using Reinforcement Learning Agent

According to various embodiments described below, an artificial intelligence (AI) agent is employed to generate one or more radiation treatment plans based on information included in a planning directive. The AI agent is trained, via reinforcement learning (RL), to determine certain actions to perform that facilitate generation of higher quality radiation treatment plans by an optimization software application. More specifically, in the embodiments, the actions performed by the AI agent include modifications to one or more dose-volume objectives or dose-volume objective parameters for a candidate radiation treatment plan. For example, actions included in the action space of the AI agent may include: repositioning a dose-volume objective curve for a particular dose-volume objective, modifying a minimum dose distribution within a target volume, modifying a maximum dose distribution within an OAR that is proximate the target volume, modifying a factor (such as a weighting factor) included in a cost function that quantifies a penalty for a radiation-delivery treatment plan failing to achieve a dose-volume objective, and the like.

The AI agent selects actions based on an action policy that is learned by the AI agent for maximizing a reward function to improve a radiation-delivery treatment plan. As a result, optimization of the candidate radiation treatment plan after the actions have been performed by the AI agent enables a higher quality radiation treatment plan to be generated by the optimization software application. In some embodiments, training of the AI agent includes learning an action policy that indicates actions for maximizing or otherwise increasing a value of a reward function associated with a radiation treatment plan. The reward function is based on a function of one (or typically multiple) dose-volume objectives, such as target coverage, sparing of OARs, homogeneity of dose applied to the planning target volume, and conformity of the region receiving a prescribed dose to the planning target volume, among others. Consequently, the reward function may be a broader concept than the cost function employed in conventional optimizer applications.

Figure 5:
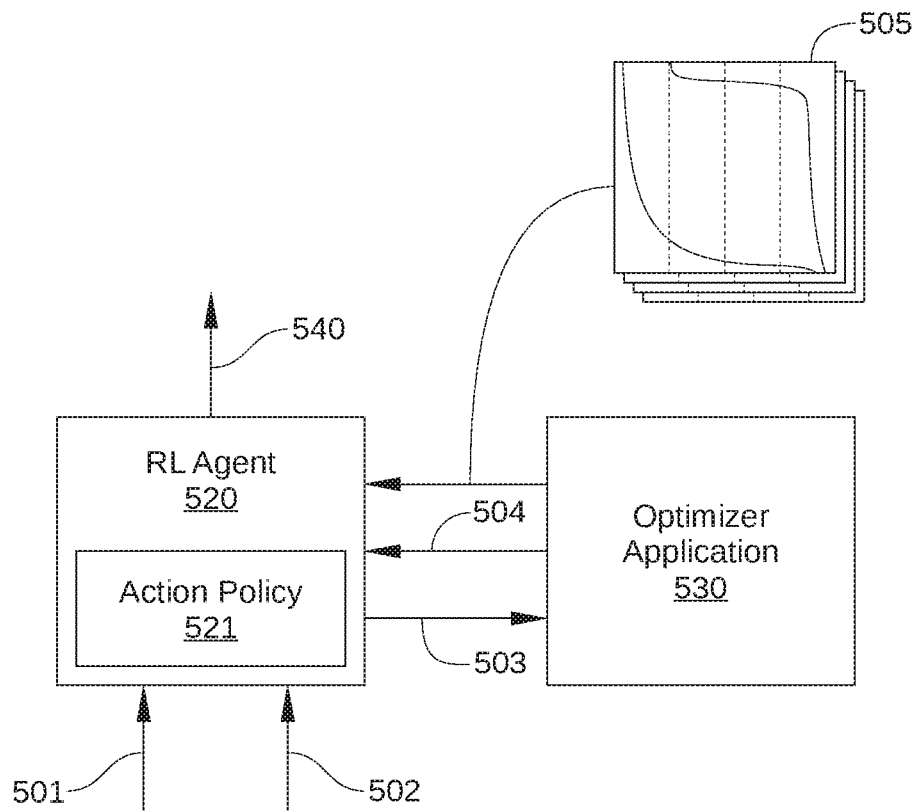
FIG. 5 is a block diagram of a treatment plan optimization system configured to generate an optimized radiation treatment plan, according to various embodiments of the present disclosure.

FIG. 5 is a block diagram of a treatment plan optimization system 500 configured to generate an optimized radiation treatment plan 540, according to various embodiments of the present disclosure. Treatment plan optimization system 500 includes a reinforcement learning (RL) agent 520 and an optimizer application 530. After appropriate training via a reinforcement learning process, RL agent 520 is configured to interact with optimizer application 530 to generate optimized radiation-delivery treatment plan 540. In some embodiments, the optimized radiation-delivery treatment plan 540 generated by treatment plan optimization system 500 can exceed the quality of a plan or plans employed to train RL agent 520.

Optimizer application 530 can be or can include a conventional treatment planning optimization software application or algorithm, such as RapidPlan™, available from Varian Medical Systems of Palo Alto, Calif. As such, optimizer application 530 is configured to enable a dosimetrist or other treatment planner to generate a new radiation delivery treatment plan for a patient that achieves the goals included in the treatment planning directive for the patient. Such goals can include one or more dose-volume objectives, such as tumor coverage, OAR and normal tissue sparing goals, and the like. Generally, optimizer application 530 employs an iterative process to determine one or more treatment beam geometries that optimize and/or otherwise select a dose distribution that satisfies the goals included in the treatment planning directive for the patient.

RL agent 520 is configured to provide inputs 503 to optimizer application 530 that enable optimizer application 530 to generate one or more treatment plans for a patient that are higher quality than treatment plans generated by a human planner interacting with a conventional optimizer application. More specifically, the one or more treatment plans generated by optimizer application 530 may not only achieve certain goals included in a treatment planning directive for the patient. For example, in an embodiment, a treatment plan generated by optimizer application 530 based on inputs 503 from RL agent 520 may exceed one or more minimum-threshold treatment goals (such as a minimum required dose in a target volume) and/or fall below one or more maximum allowable goal thresholds (such as a maximum allowable dose in an OAR). Thus, such a treatment plan is of higher quality than a treatment plan that merely meets certain goals.

In some embodiments, RL agent 520 receives patient-specific planning information 501, generates an initial treatment plan for the patient based on such information, and provides the initial treatment plan to optimizer application 530 as an input 503. Alternatively or additionally, in some embodiments, RL agent 520 receives an existing treatment plan 502 for the patient, such as a treatment plan generated at an earlier phase of the treatment of the patient. In such embodiments, RL agent 520 generates a modified treatment plan by modifying the existing treatment plan 502 according to embodiments described below, then provides the modified treatment plan to optimizer software application 530 as an input 503. For example, detection of a change of one or more patient volumes of interest may indicate a modification may be beneficial of an existing treatment plan by treatment plan optimization system 500, such as when a GTV is determined to change in size and/or change location relative to a specific structure (e.g., an OAR).

In some embodiments, patient-specific planning information 501 can include information that enables construction of a treatment plan, such as a delineated target of the planned radiation therapy based on a treatment planning CT and on information included in the treatment planning directive. For example, one or more of the GTV, the CTV, the ITV, and/or the PTV may be delineated on two-dimensional slices from the reconstructed volume imaged in the planning treatment CT. Further, one or more OARs may be similarly delineated. In some instances, a radiation oncologist performs one or more of these delineations manually via a display screen. Generally, the radiation oncologist delineates the various target volumes based on visual cues in each two-dimensional slice of the reconstructed volume as well as on personal training and experience. Alternatively, in some instances, the radiation oncologist can be assisted in segmenting the one or more anatomical structures (GTV, CTV, ITV, PTV, OAR, etc.) by a software application configured to automatically generate a segmentation of the GTV, the PTV, and the like.

In some embodiments, patient-specific planning information 501 further includes one or more treatment goals, dose-volume objectives and/or dose-volume objective parameters for the segmented target regions and/or OARs, such as information included in a treatment planning directive for a particular patient. Thus, in some embodiments, patient-specific planning information 501 can include an upper dose-volume objective that limits dose in a particular structure (for example, no more than 20% of the particular structure may receive more than 25 Gy"), a lower dose-volume objective that defines a desired dose level in a particular target structure (for example, "at least 70% of the structure must receive at least 20 Gy"), a homogeneity of dose within the GTV, CTV, or PTV, a conformity index value that indicates conformity of a particular region receiving a prescribed dose to the PTV, and the like.

In operation, RL agent 520 generates inputs 503, which can include a treatment plan to be optimized by optimizer application 530. Additionally or alternatively, inputs 503 include one or more dose-volume objectives that enable optimizer application 530 to modify an existing treatment plan to be optimized. Optimizer application 530 then performs an optimization process on the treatment plan that is provided by RL agent 520. Alternatively, optimizer application 530 modifies an existing treatment plan according to the inputs provided by RL agent 520. For example, in embodiments in which inputs 503 include one or more dose-volume objectives, optimizer application 530 modifies the existing treatment plan and performs the optimization process on the modified treatment plan. That is, a candidate treatment plan is generated by optimizer application 530 according to the new dose-volume objectives provided by RL agent 520.

In an optimization process, optimizer application 530 typically begins with some initial set of parameter settings, iteratively adjusts one or more of the parameter settings, and quantitatively assesses the relative worth of the adjusted plan, for example with via a cost function that weights the relative value of each treatment goal of the treatment plan being optimized. In the iterations, various aspects of the treatment plan being optimized are varied, such as collimator leaf settings for each of a plurality of X-ray source angles, X-ray source levels for each of the plurality of X-ray source angles, etc. Such an iterative approach enables a certain level of exploration of various solutions that can satisfy each treatment goal of the treatment plan differently. It is noted that the "optimized" plan results from such an optimization process is not assumed to be the best possible (or optimal) plan that is superior to any other alternative. Instead, the term "optimized" plan, as used herein, references a treatment plan that is improved over the initial plan prior to the optimization process.

Upon completion of the optimization process, optimizer application 530 generates a candidate treatment plan 504 and/or dose-volume information 505 associated with the candidate treatment plan 504. Candidate treatment plan 504 is a radiation-delivery treatment plan for the patient that is typically a clinically acceptable treatment plan, but may be improved by one or more modifications by RL agent 520. In some embodiments, dose-volume information 505 includes one or more dose-volume histograms or data that can be formulated into one or more dose-volume histograms. One example of a dose-volume histogram that can be included in dose-volume information 505 is described below in conjunction with FIG. 6.

Figure 6:
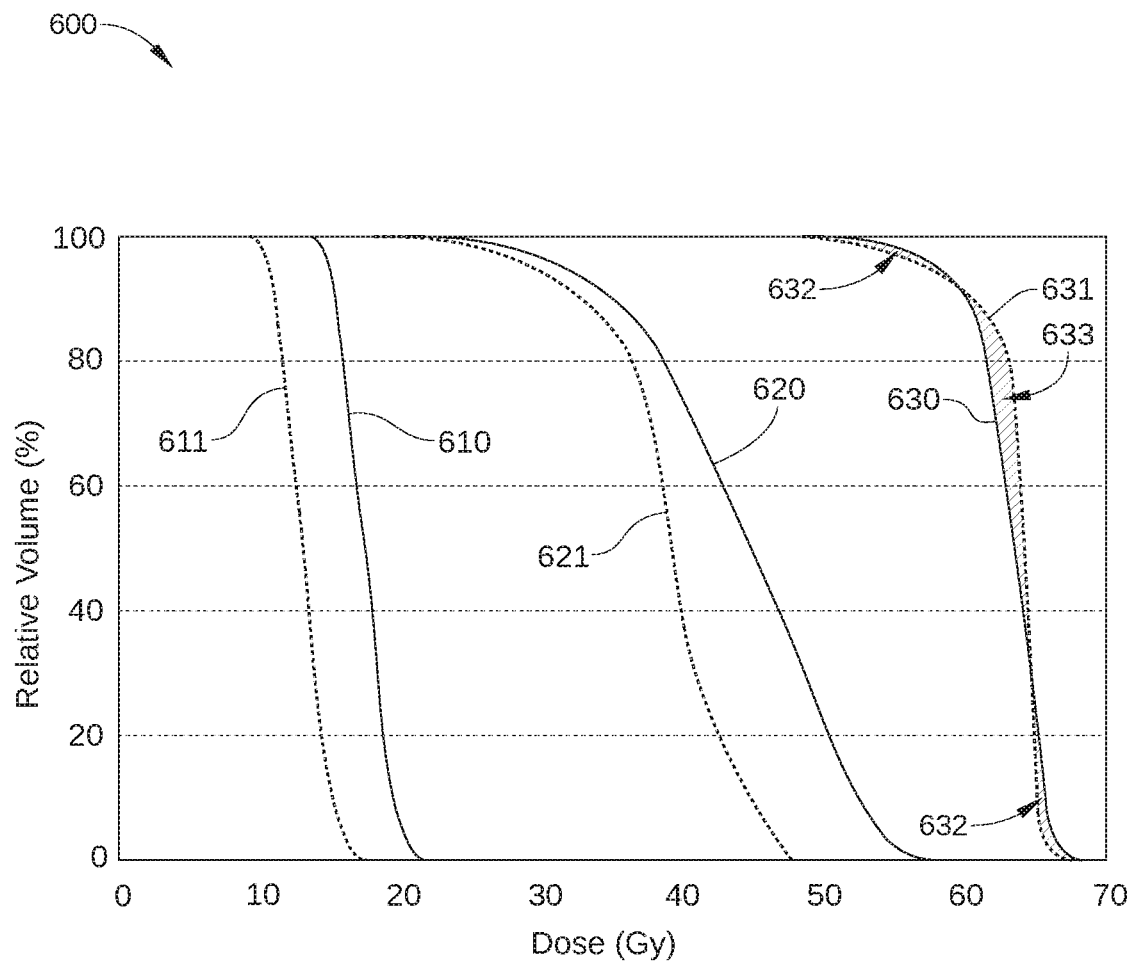
FIG. 6 illustrates a dose-volume histogram (DVH), according to various embodiments of the present disclosure.

FIG. 6 illustrates a dose-volume histogram (DVH) 600, according to various embodiments of the present disclosure. DVH 600 relates, in a two-dimensional format, the predicted radiation dose for a specific treatment plan to a particular tissue volume (such as a PTV, GTV, OAR, or other structure). For example, DVH 600 can indicate predicted radiation dose for one or more structures after implementation of a particular treatment plan, such as candidate treatment plan 504 of FIG. 5. Consequently, DVH 600 enables the predicted radiation dose for the one or more structures for multiple treatment plans to be compared.

A DVH includes dose information for a plurality of dose bins and can be implemented as either a differential DVH or a cumulative DVH. In the embodiment illustrated in FIG. 6, DVH 600 is a cumulative DVH, and includes a value for a plurality of dose bins from 0 to 70 Gy that are plotted along a horizontal axis. In DVH 600, column height for each bin (for example, 0 Gy, 1 Gy, 2 Gy, etc.) indicates a volume of a particular structure receiving greater than or equal to that dose value. For example, the column height of the second bin (1 Gy) represents the volume of the particular structure receiving greater than or equal to that dose. Thus, with a large number of small bin sizes, each dose-volume objective included in DVH 600 substantially appears to be a smooth curve.

In the embodiment illustrated in FIG. 6, DVH 600 includes dose-volume objectives for several different structures: a dose-volume objective 610 for a first OAR, a dose volume objective 620 for a second OAR, and a dose-volume objective 630 for a target region, such as a PTV. In other embodiments, DVH 600 can include more or fewer dose-volume objectives. Dose-volume objective 610 and dose volume objective 620 are each associated with an OAR and, as such, indicate a maximum allowable dose distribution in the associated OAR. That is, dose-volume objective 610 indicates a maximum allowable dose distribution within an organ at risk or other structure that is proximate the target region and dose volume objective 620 indicates a maximum allowable dose distribution within another organ at risk or other structure that is proximate the target volume. By contrast, dose-volume objective 630 is associated with a target region, and consequently indicates a target minimum dose threshold for radiation treatment of the PTV. In light of the above, an ideal treatment plan satisfies dose-volume objective 630 for all dose bins while the OARs or structures associated with dose-volume objective 610 and dose volume objective 620 receive zero dose. In practice, implementation of a candidate treatment plan necessarily causes the OARs or structures associated with dose-volume objective 610 and dose volume objective 620 to receive some non-zero dose. Further, some or all of the dose bins of dose-volume objective 630 may not be satisfied. That is, there is a trade-off involved in satisfying dose-volume objective 630 and minimizing or otherwise reducing the dose received by OARs and other critical structures. This trade-off is illustrated by the dose curves 611, 621, and 631, which are described below.

For each of dose-volume objectives 610, 620, and 630, DVH 600 further includes a dose curve (dashed lines) indicating a predicted dose for the associated structure when a particular treatment plan is implemented, such as candidate treatment plan 504 of FIG. 5. Thus, DVH 600 further includes a dose curve 611 for the region or structure associated with dose-volume objective 610, a dose curve 621 for the region or structure associated with dose-volume objective 620, and a dose curve 631 for the region or structure associated with dose-volume objective 630.

As shown, in the instance illustrated in FIG. 6, dose curve 631 is less than ideal, since dose-volume objective 630 is not met for all dose bins. Instead, there are deviations 632 and 633 (indicated by a cross-hatched area) between dose curve 631 and dose-volume objective 630, where dose curve 631 varies from dose-volume objective 630. Deviations 632 correspond to where dose curve 631 falls below dose-volume objective 630 and deviations 633 correspond to where dose curve 631 exceeds dose-volume objective 630. Further, dose curve 611 is also less than ideal. Specifically, even though dose curve 611 indicates that the candidate treatment plan associated with DVH 600 is less than the maximum allowable dose distribution in the associated OAR in all dose bins, at least some portion of the associated OAR receives at least some dose. Similarly, dose curve 621 is also less than ideal, since at least some portion of the OAR associated with dose-volume objective 620 receives at least some dose. Consequently, even though the candidate treatment plan associated with DVH 600 (such as candidate treatment plan 504) may be clinically acceptable, the candidate treatment plan can potentially be further improved by RL agent 520 interacting with optimizer application 530 as described below.

In the embodiments, an RL agent changes the cost function associated with the current candidate treatment plan by changing the dose corresponding to one or more dose-volume objectives. Such modification of dose-volume objectives changes the cost function because each unique set of objective parameters defines a distinct cost function. For example, in some embodiments, in a dose-volume histogram plane, a dose-volume objective can be moved to the right or left in DVH 600 by increasing or decreasing an appropriate dose parameter of that dose-volume objective, respectively. Likewise, in some embodiments, a dose-volume objective can be moved up or down in DVH 600 by increasing or decreasing the volume % of that dose-volume objective.

Returning to FIG. 5, RL agent 520 evaluates candidate treatment plan 504 and/or dose-volume information 505 to determine whether candidate treatment plan 504 can be further improved. Thus, in some embodiments, RL agent 520 evaluates candidate treatment plan 504 based on dose-volume information 505. In some embodiments, RL agent 520 determines a current state of candidate treatment plan 504 as provided by optimizer application 530. In such embodiments, the current state of candidate treatment plan 504 is determined using dose-volume information 505. For example, in such embodiments, a state of candidate treatment plan 504 may be based on a dictionary containing OAR and target structures (e.g., GTV, CTV, PTV, etc.) as keys, where values for each key make up the current state of candidate treatment plan 504. In some embodiments, the value for a key is generated from the corresponding dose-volume information (such as a DVH curve) for each OAR and target structure. In such embodiments, the current state of candidate treatment plan 504 may be based on values for each OAR and target structure, where each value is derived from deviations of a dose curve from a corresponding dose-volume objective. For example, in one embodiment, one value that contributes to the current state of candidate treatment plan 504 is derived from deviations 632 and 633 (shown in FIG. 6) of dose curve 631 from dose-volume objective 630.

Alternatively or additionally, in some embodiments, RL agent 520 evaluates candidate treatment plan 504 based on other quantitative metrics indicating a quality of candidate treatment plan 504. For example, in some embodiments, RL agent 520 evaluates candidate treatment plan 504 based on a conformity index of a target volume, a calculation of a reward function similar to that employed during a training process for RL agent 520, and/or other quantitative metrics.

After RL agent 520 evaluates candidate treatment plan 504 based on dose-volume information 505, RL agent 520 selects one or more actions for modifying candidate treatment plan 504 using an action policy 521 that has been learned by RL agent 520 during a training process. In some embodiments, RL agent 520 selects the one or more actions based on the current state of candidate treatment plan 504, which is based on values for each OAR and target structure. In such embodiments, RL agent 520 recognizes the current state of candidate treatment plan 504 and selects one or more actions that action policy 521 indicates have resulted in a high reward during the training process. That is, for each state of a candidate treatment plan that is tested during the reinforcement learning process, RL agent 520 stores a resultant reward for each action that is performed on the candidate treatment plan. In this way, an action policy 521 is generated during a reinforcement learning process for RL agent 520.

In the reinforcement learning process, a resultant reward is observed for various actions performed on a candidate treatment plan by RL agent 520 when the candidate treatment plan is in a particular state. The resultant reward is determined for a particular action by performing the action on the candidate treatment plan (i.e., modifying the candidate treatment plan), performing an optimization process on the modified candidate treatment plan with optimizer application 530, and quantifying changes in the quality of the newly optimized treatment plan. In some embodiments, the quality of the newly optimized treatment plan is quantified via a reward function that reflects or is otherwise based on some or all of the treatment goals associated with the candidate treatment plan. In this way, an entry in action policy 521 is generated. That is, each action and associated reward function value contributes to action policy 521.

In some embodiments, the reward function can be a function of one or more factors, including: target coverage; OAR sparing; a homogeneity of dose within the GTV, CTV, and/or PTV; a conformity index value that indicates conformity of a particular region receiving a prescribed dose to the PTV; and computational efficiency, among others. In some embodiments, improvements by the candidate treatment plan with respect to one or more of the above factors is more highly rewarded than improvements by the candidate treatment plan with respect to other of the above factors. For example, some or all of the factors on which the reward function is based may have a weighting factor associated therewith, where some or all of such weighting factors can be different values. Thus, in such embodiments, one or more of the above factors has a weighted contribution to the reward function. Alternatively or additionally, in some embodiments, achievement by the candidate treatment plan of a threshold condition for a particular factor is more highly rewarded than exceeding the threshold condition for the particular factor. For example, in an embodiment, achieving the dosimetric guidelines for target coverage (e.g., a minimum dose threshold) and OAR sparing (e.g., a maximum dose threshold) is highly rewarded compared to exceeding such guidelines.

In some embodiments, homogeneity of the PTV is accounted for by rewarding smaller values of $D_5$-$D_{95}$, where $D_X$ represents the dose corresponding to X % of volume. In some embodiments, the conformity index is defined as the volume of the iso-surface of the prescription dose divided by the volume of the corresponding PTV. In some embodiments, more reward is generated for smaller values of |conformity index−1|. In some embodiments, efficiency of a candidate treatment plan is measured as the number of times that RL agent 520 triggers optimizer application 530 before a clinically acceptable plan is generated.

In some embodiments, a different action policy 521 is generated for different clinical scenarios. For example, in some embodiments, a unique action policy 521 is developed via a reinforcement learning process for each different part of the anatomy. Additionally or alternatively, in some embodiments, a unique action policy 521 is developed via a reinforcement learning process for each of a plurality of different categories of patient. For example, in such embodiments, a different action policy 521 may be developed based on patient gender, patient age, etc. Additionally or alternatively, in some embodiments, a unique action policy 521 is developed via a reinforcement learning process for a particular radiation therapy system. Additionally or alternatively, in some embodiments, a unique action policy 521 is developed for any combination of two or more of the above clinical scenarios.

In some embodiments, an action space for RL agent 520 includes generating a modified dose-volume objective and causing optimizer application 530 to generate another candidate treatment plan 504 that meets the modified dose-volume objective. That is, RL agent 520 modifies at least one dose-volume objective parameter of the current candidate treatment plan 504 and causes optimizer application 530 to perform an optimization process on the now modified version of candidate treatment plan 504. Various dose-volume objective parameters that can be changed by RL agent 520 are described below.

Figure 7:
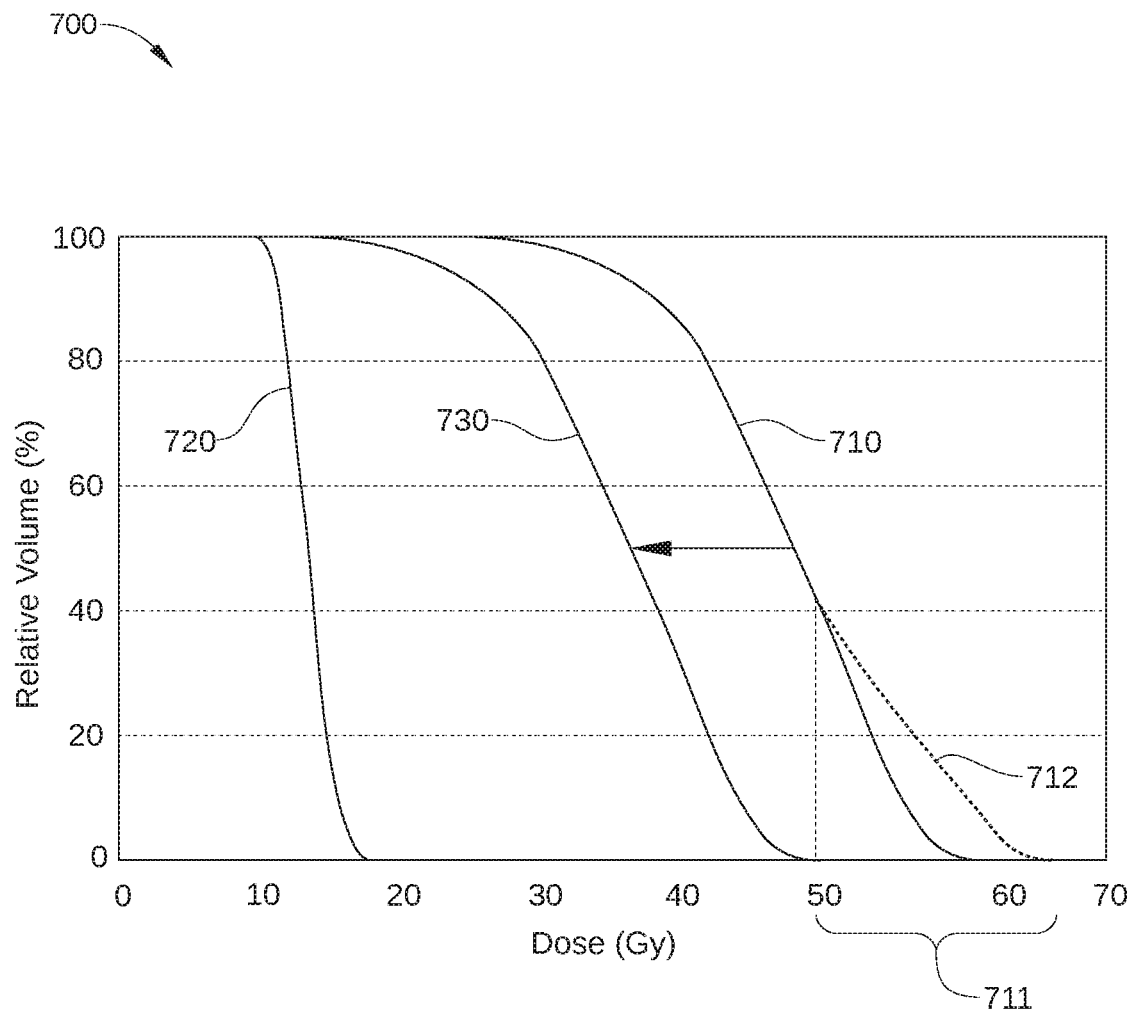
FIG. 7 illustrates a DVH and certain changeable dose-volume objective parameters, according to various embodiments of the present disclosure.

FIG. 7. illustrates a DVH 700 and certain changeable dose-volume objective parameters, according to various embodiments of the present disclosure. DVH 700 is a cumulative DVH, and includes a dose-volume objective 710 for an OAR (not shown). According to various embodiments, one or more dose-volume objective parameters can be modified by RL agent 520 of FIG. 5 to generate a modified dose-volume objective that RL agent 520 then includes in a treatment plan for further optimization. For example, in some embodiments, a dose-volume objective parameter for dose-volume objective 710 that can be modified includes a dose value for one or more of the dose bins of DVH 700. Thus, in such embodiments, RL agent 520 generates a modified dose-volume objective for the OAR by modifying the dose value for one or more dose bins of DVH 700. In one such embodiment, RL agent 520 modifies the dose values of a portion of the dose bins of dose-volume objective 710 (for example, dose bins 711). In so doing, RL agent 520 generates a modified dose-volume objective for the OAR that includes a modified segment 712 (dashed line) that is different from a portion of dose-volume objective 710. In another such embodiment, RL agent 520 modifies the dose values of dose-volume objective 710 for all dose bins, thereby generating a completely different dose-volume objective 720 for the OAR. In yet another such embodiment, RL agent 520 shifts the dose values of each dose bin of dose-volume objective 710 by the same number of dose bins and in the same direction. In such an embodiment, RL agent 520 generates a different dose-volume objective 730 for the OAR that is uniformly shifted toward either higher doses or lower doses than dose-volume objective 710.

Returning to FIG. 5, in some embodiments, a dose-volume objective parameter that is modified by RL agent 520 is a parameter that modifies a cost function employed in the optimization process performed by optimizer application 530. In some embodiments, a dose value of a dose-volume objective (as described above in conjunction with FIG. 7) is such a dose-volume objective parameter. Alternatively or additionally, in some embodiments, a dose-volume objective parameter that is modified by RL agent 520 is a weighting factor, where the weighting factor modifies a contribution to the cost function of one dose-volume objective relative to a contribution to the cost function of another dose-volume objective. Thus, in such an embodiment, RL agent 520 modifies a subsequent optimization process performed by optimizer application 530 by changing relative importance (or weight) of different dose-volume objectives. For example, by increasing the importance of a first dose-volume objective relative to a second dose-volume objective that conflicts with the first dose-volume objective, a higher quality treatment plan can be generated by optimizer application 530.

In some embodiments, when RL agent 520 evaluates candidate treatment plan 504 and/or dose-volume information 505 and determines that candidate treatment plan 504 meets a certain end condition or conditions, RL agent 520 generates or otherwise outputs an optimized treatment plan 540. Such end conditions can include a maximum threshold number of interaction iterations occurring between RL agent 520 and optimizer application 530, a determination that candidate treatment plan 504 is a clinically acceptable plan, a determination that candidate treatment plan 504 meets one or more additional quality criteria (such as exceeding a certain clinical goal or goals), and the like.

Figure 8:
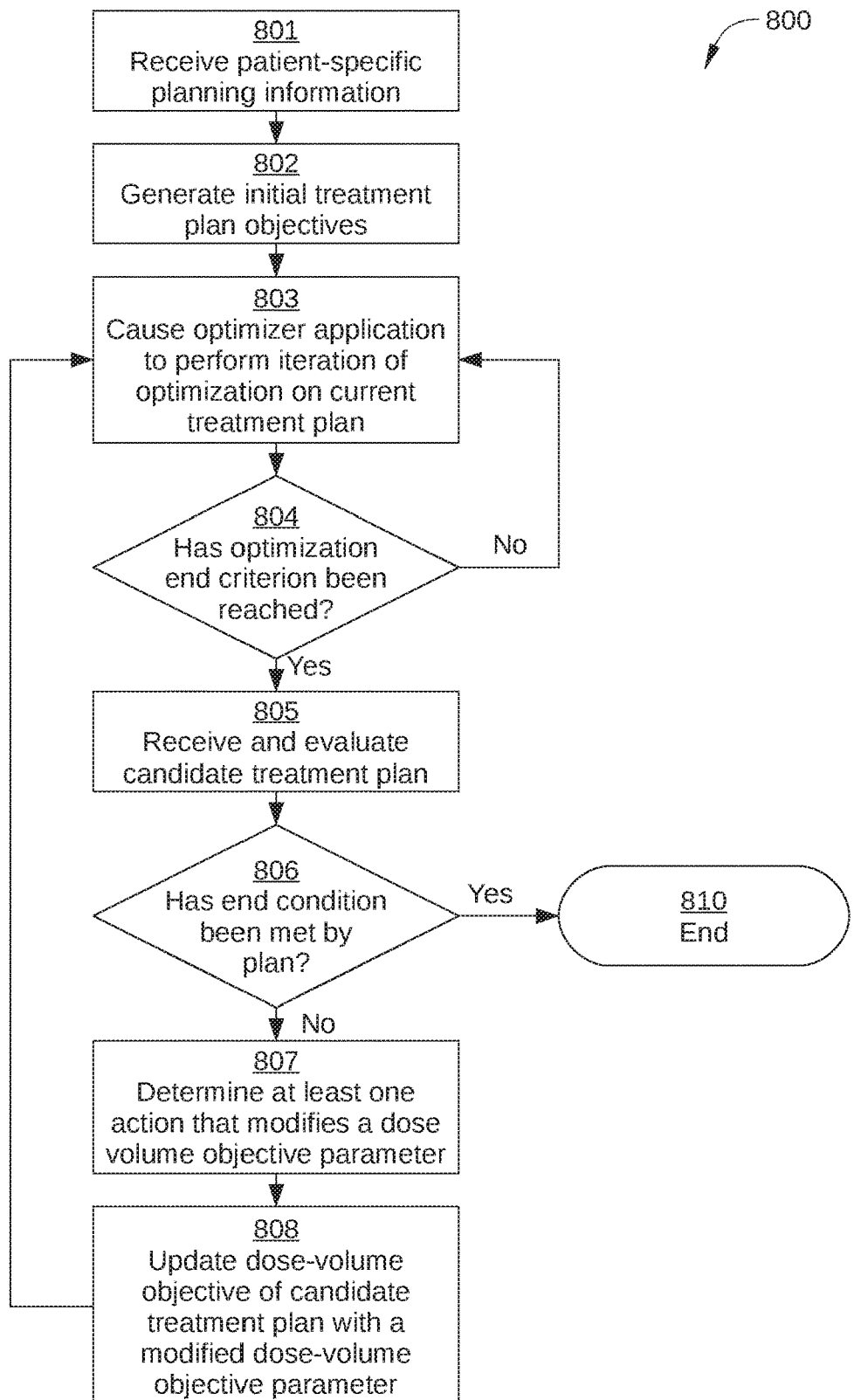
FIG. 8 sets forth a flowchart of an example optimization process for a treatment plan, according to one or more embodiments of the present disclosure.

FIG. 8 sets forth a flowchart of an example optimization process for a treatment plan, according to one or more embodiments of the present disclosure. The method may include one or more operations, functions, or actions as illustrated by one or more of blocks 801-810. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the processes and systems of FIGS. 1-7, persons skilled in the art will understand that any suitably configured system can perform the optimization process described herein. In some instances, the method is performed prior to any radiation treatment of the patient. In other instances, the method is performed in response to changes being detected in size, shape, and/or relative positioning of a target volume and/or OAR, in which case the current treatment plan for the patient can be modified appropriately.

An optimization process 800 begins at step 801, when RL agent 520 receives patient-specific planning information 101 and/or an existing treatment plan 502 for a patient.

In step 802, RL agent 520 generates initial treatment plan objectives, such as dose-volume objectives, if no existing treatment plan 502 is available. In some embodiments, the treatment plan objectives and/or dose-volume objectives generated in step 802 are based on a default treatment plan and/or on treatment goals included in patient-specific planning information 101.

It is noted that such initial treatment plan objectives define a specific cost function for optimizer application 530. That is, the cost function that is used by optimizer application 530 to optimize a particular treatment plan is a function of the specific values included in each treatment plan objective. For example, one such treatment plan objective may be an upper dose-volume objective used to limit the dose in a given structure (e.g., "no more than 20% of the structure may receive more than 25 Gy"). In another example, one such treatment plan objective may be a lower dose-volume objective used to define a target dose level in a target structure (e.g., "at least 70% of the target structure must receive at least 20 Gy").

In step 803, RL agent 520 causes optimizer application 530 to perform an iteration of optimization of the current treatment plan using the current dose-volume objectives. For example, in a first iteration of step 803, RL agent 520 generally causes optimizer application 530 to perform the iteration of optimization on existing treatment plan 502, if available. By contrast, in subsequent iterations of step 803, RL agent 520 generally causes optimizer application 530 to perform the iteration of optimization on a modified candidate treatment plan 504.

In step 804, optimizer application 530 determines whether an optimization end criterion or criteria have been reached.

If yes, method 800 proceeds to step 805; if no, method 800 returns to step 803 and optimizer application 530 performs another iteration of optimization on the current candidate treatment plan.

In step 805, RL agent 520 receives candidate treatment plan 504 and/or dose-volume information 505 associated with the candidate treatment plan 504. RL agent 520 then evaluates candidate treatment plan 504. In some embodiments, RL agent 520 evaluates candidate treatment plan 504 based on the current state of candidate treatment plan 504. For example, in some embodiments, RL agent 520 performs the evaluation of the candidate treatment plan for the target volume by comparing at least one dose-volume distribution generated by the candidate treatment plan to a corresponding dose-volume objective included in or otherwise associated with the candidate treatment plan.

In step 806, RL agent 520 determines whether an end condition or conditions are met by candidate treatment plan 504. If yes, method 800 proceeds to step 810 and terminates and an optimized radiation treatment plan 540 is generated; if no, method 800 proceeds to step 807.

In step 807, based on the current state of candidate treatment plan 504, RL agent 520 determines at least one action that modifies a dose-volume objective parameter of a dose-volume objective for the candidate treatment plan. For example, in some embodiments, the dose-volume objective parameter modified by the action can be one of a minimum dose distribution within a target volume (e.g., a GTV, a CTV, an ITV, a PTV, etc.), a maximum dose distribution within an OAR that is proximate the target volume, a factor included in a cost function that quantifies a penalty for a radiation-delivery treatment plan failing to achieve a dose-volume objective, etc. In some embodiments, RL agent 520 determines multiple actions that each modify a dose-volume objective parameter.

In some embodiments, RL agent 520 determines the at least one action based on the current state of candidate treatment plan 504 and on action policy 521. In such embodiments, RL agent 520 selects the at least one action from an action space of RL agent 520. In some embodiments, examples of actions included in such an action space include: changing a threshold value associated with a particular dose-volume objective of the candidate treatment plan, repositioning, on a dose-volume histogram, a dose-volume curve associated with a particular dose-volume objective of the candidate treatment plan, and modifying a weighting factor associated with a particular dose-volume objective of the candidate treatment plan.

In step 808, RL agent 520 generates a modified dose-volume objective by performing the action determined in step 807. Thus, in step 808, RL agent 520 updates at least one dose-volume objective of the candidate treatment plan with a modified dose-volume objective parameter. Method 800 then returns to step 803, and optimizer application 530 performs an iteration of optimization on the now modified treatment plan.

Training a Reinforcement Learning Agent

According to various embodiments described herein, an RL agent learns an action policy to adaptively adjust the dose-volume objectives of a candidate treatment plan to maximize or otherwise increase a cumulative reward or other output from a reward function. As is well-known in the art, in training an RL agent, the RL agent takes actions in an environment, and the results of the action is observed and quantified as a reward associated with a certain state of the environment. The reward and associated state are then fed back to the RL agent, which repeats the process with one or more different actions. According to various embodiments, to facilitate the training of RL agent 520 of FIG. 5, a reward function is employed that is based on clinical goals of a radiation-delivery treatment plan, as described below.

In some embodiments, an action space for an RL agent includes moving a specific dose-volume objective, for example either to the right or left. Additionally, in some embodiments, the action space further includes running or stopping optimizer application 530. In an example embodiment, the dose-volume objective can be moved between 0 and 100 Gy with the step size of 0.1 Gy. In the embodiment, the agent is in state s, takes action a, and observes the next state, s'. Then the immediate reward is described by Equation 1: r=v(s')−v(s), where v(•) is the state value function. One embodiment of a state value function for a particular structure, such as an OAR or a PTV, is described below.

For the structure, $v(d_j)$ denotes the volume % at the dose $d_j \in [0,1000]$ (dGy) in a particular dose-volume objective curve, and $\hat{v}(d_j)$ denotes the volume % corresponding to the dose $d_j$ at state s. A quality measure based on an upper clinical goal ($d^{cg}$, $v^{cg}$) for the structure is described by Equation 2:

$$u^{cg}(s) = -\exp[\hat{v}_s(d^{cg}) - v^{cg}] \qquad (2)$$

A quality measure based on a lower clinical goal ($d^{cg}$, $v^{cg}$) for the structure is described by Equation 3:

$$u^{cg}(s) = -\exp[-\hat{v}_s(d^{cg}) + v^{cg}] \qquad (3)$$

When the structure is an OAR, a quality measure based on a DVH of an OAR is described by Equation 4:

$$u^{oar}(s) = -\frac{1}{D} \sum_{d_j=0}^{D} \exp[\hat{v}_s^{oar}(d_j) - v^{oar}(d_j)] \qquad (4)$$

where D denotes the number of points in the dose axis after discretization. For example, if the dose axis is ranging from 0 to 100 Gy and discretization step is 0.1, then D=1000.

A quality measure for a target structure with the prescribed dose $D_{pr}$ is described by Equation 5:

$$u^{ptv}(s) = -\frac{1}{D}\left\{\sum_{d_j}^{D_{pr}} \exp[-\hat{v}_s^{ptv}(d_j) + 100] + \sum_{d_j=D_{pr}+1}^{D} \exp[\hat{v}_s^{ptv}(d_j)]\right\} \qquad (5)$$

In light of the above, a state value function can defined by Equation 6:

$$(6)$$

$$v(s) = \log\left\{\frac{1}{n^{oar}+n^{ptv}+n^{cg}}\left[\sum_{i=1}^{n^{oar}} w_i^{oar} u_i^{oar}(s) + \sum_{i=1}^{n^{ptv}} w_i^{ptv} u_i^{ptv}(s) + \sum_{i=1}^{n^{cg}} w_i^{cg} u_i^{cg}(s)\right]\right\}$$

where $n^{oar}$, $n^{ptv}$, and $n^{cg}$ denote the number of OARs, targets, and clinical goals respectively, with weights $w^{oar}$, $w_{ptv}$ and $w^{cg}$ assigned by a planner. In alternative embodiments, the state value function can contain a term based on a spatial evaluation of dose-volume objectives in a treatment plan and the dose distribution based on the current solution.

Figure 9:
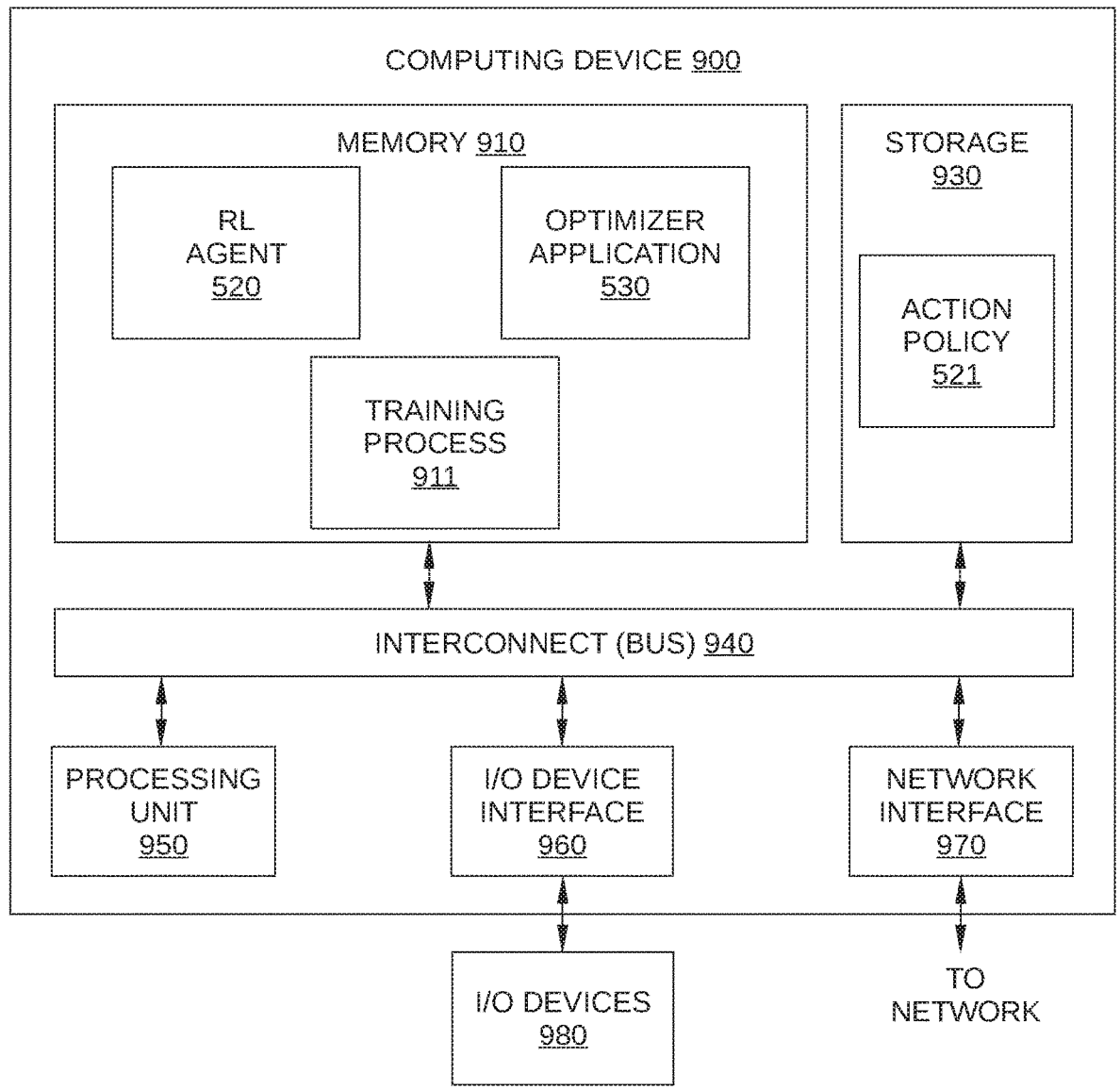
FIG. 9 is an illustration of computing device configured to perform various embodiments of the present disclosure.

FIG. 9 is an illustration of computing device 900 configured to perform various embodiments of the present disclosure. Computing device 900 may be a desktop computer, a laptop computer, a smart phone, or any other type of computing device suitable for practicing one or more embodiments of the present disclosure. In operation, computing device 900 is configured to perform RL agent 520, optimizer application 530, and/or a reinforcement learning training process 911, as described herein. It is noted that the computing device described herein is illustrative and that any other technically feasible configurations fall within the scope of the present disclosure.

As shown, computing device 900 includes, without limitation, an interconnect (bus) 940 that connects a processing unit 950, an input/output (I/O) device interface 960 coupled to input/output (I/O) devices 980, memory 910, a storage 930, and a network interface 970. In some embodiments, action policy 521 resides in storage 930. Processing unit 950 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 950 may be any technically feasible hardware unit capable of processing data and/or executing software applications, including RL agent 520, optimizer application 530, and/or reinforcement learning training process 911.

I/O devices 980 may include devices capable of providing input, such as a keyboard, a mouse, a touch-sensitive screen, and so forth, as well as devices capable of providing output, such as a display device and the like. Additionally, I/O devices 980 may include devices capable of both receiving input and providing output, such as a touchscreen, a universal serial bus (USB) port, and so forth. I/O devices 980 may be configured to receive various types of input from an end-user of computing device 900, and to also provide various types of output to the end-user of computing device 900, such as displayed digital images or digital videos. In some embodiments, one or more of I/O devices 980 are configured to couple computing device 900 to a network.

Memory 910 may include a random access memory (RAM) module, a flash memory unit, or any other type of memory unit or combination thereof. Processing unit 950, I/O device interface 960, and network interface 970 are configured to read data from and write data to memory 910. Memory 910 includes various software programs that can be executed by processor 950 and application data associated with said software programs, including RL agent 520, optimizer application 530, and/or reinforcement learning training process 911.

Figure 10:
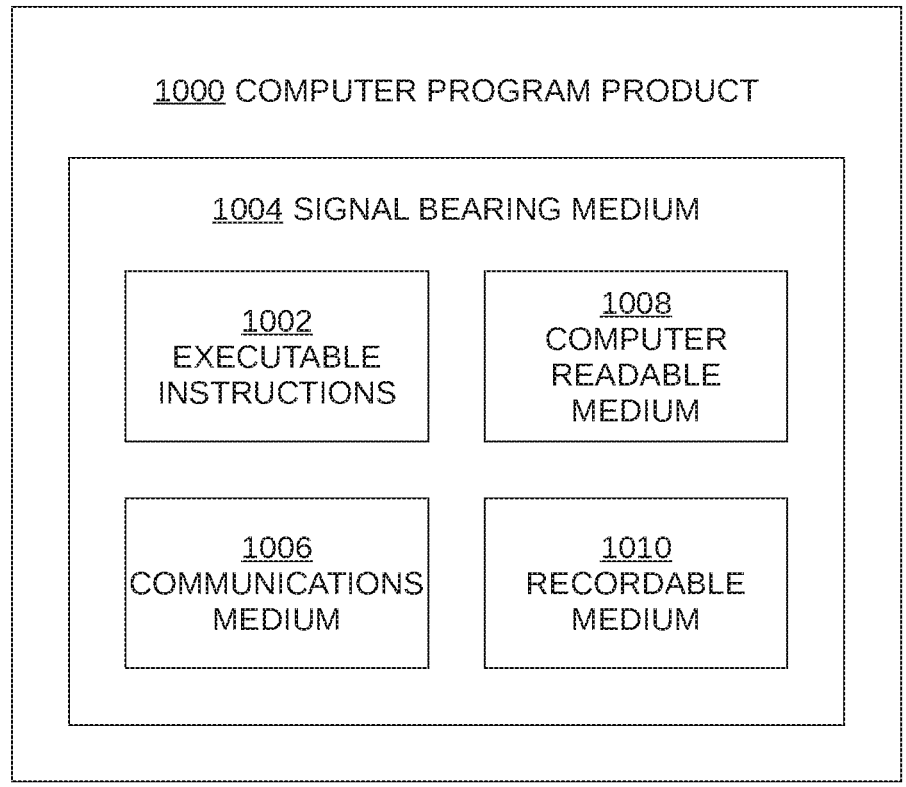
FIG. 10 is a block diagram of an illustrative embodiment of a computer program product for implementing a method for segmenting an image, according to one or more embodiments of the present disclosure.

FIG. 10 is a block diagram of an illustrative embodiment of a computer program product 1000 for implementing one or more embodiments of the present disclosure. Computer program product 1000 may include a signal bearing medium 1005. Signal bearing medium 1004 may include one or more sets of executable instructions 1002 that, when executed by, for example, a processor of a computing device, may provide at least the functionality described above with respect to FIGS. 1-9.

In some implementations, signal bearing medium 1004 may encompass a non-transitory computer readable medium 1008, such as, but not limited to, a hard disk drive, a Compact Disc (CD), a Digital Video Disk (DVD), a digital tape, memory, etc. In some implementations, signal bearing medium 1004 may encompass a recordable medium 1010, such as, but not limited to, memory, read/write (R/W) CDs, R/W DVDs, etc. In some implementations, signal bearing medium 1004 may encompass a communications medium 1006, such as, but not limited to, a digital and/or an analog communication medium (e.g., a fiber optic cable, a waveguide, a wired communications link, a wireless communication link, etc.). Computer program product 1000 may be recorded on non-transitory computer readable medium 1008 or another similar recordable medium 1010.

In sum, embodiments of the present disclosure facilitate optimization of a radiation-delivery treatment plan with an RL agent. The RL agent is configured to generate a radiation-delivery treatment plan that can exceed the quality of a plan or plans employed to train the RL agent. The RL agent is trained to evaluate a radiation-delivery treatment plan that is output by an optimization software application, modify one or more dose-volume objective parameters of the evaluated radiation-delivery treatment plan, and then input the modified radiation-delivery treatment plan to the optimization software application for further optimization. The RL agent adaptively adjusts the one or more dose-volume objective parameters based on an action policy learned during a reinforcement learning training process.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of generating a treatment plan for delivering radiation treatment to a target volume, the method comprising:
performing an evaluation of a first treatment plan for the target volume by comparing a dose-volume distribution based on the first treatment plan to a dose-volume objective included in a set of one or more dose-volume objectives;
based on the evaluation and on an action policy that indicates multiple actions for improving the treatment plan, selecting from the multiple actions an action that modifies at least one dose-volume objective parameter for the dose-volume objective included in the set of one or more dose-volume objectives;
generating a modified dose-volume objective by performing the action on the dose-volume objective included in the set of one or more dose-volume objectives; and
causing an optimization application to generate a second treatment plan that meets the modified dose-volume objective.

2. The computer-implemented method of claim 1, further comprising, causing the second treatment plan to be implemented via a radiation therapy system.

3. The computer-implemented method of claim 1, wherein the at least one dose-volume objective parameter comprises at least one of a minimum dose distribution within the target volume, a maximum dose distribution within an organ at risk that is proximate the target volume, or a factor included in a cost function that quantifies a penalty for a treatment plan failing to achieve the dose-volume objective.

4. The computer-implemented method of claim 3, wherein the factor included in the cost function comprises a weighting factor associated with a first dose-volume objective included in the set of one or more dose-volume objectives.

5. The computer-implemented method of claim 3, wherein the weighting factor modifies a first contribution to the cost function of the dose-volume objective included in the set of one or more dose-volume objectives relative to a second contribution to the cost function of another dose-volume objective included in the set of one or more dose-volume objective.

6. The computer-implemented method of claim 1, wherein selecting the action comprises selecting at least one action from an action space that includes changing a threshold value associated with the at least one dose-volume objective included in the set of one or more dose-volume objectives; repositioning, on a dose-volume histogram, a dose-volume curve associated with the at least one dose-volume objective included in the set of one or more dose-volume objectives; and modifying a weighting factor associated with the at least one dose-volume objective included in the set of one or more dose-volume objectives.

7. The computer-implemented method of claim 6, wherein selecting the action comprises selecting multiple actions from the action space.

8. The computer-implemented method of claim 1, further comprising:
prior to causing the optimization application to generate the second treatment plan, generating a modified treatment plan by modifying the first treatment plan with the modified dose-volume objective parameter,
wherein causing the optimization application to generate the second treatment comprises performing an optimization process on the modified treatment plan.

9. The computer-implemented method of claim 8, wherein causing the optimization application to generate the second treatment plan comprises causing the optimization application to perform at least one iteration of an optimization process on the modified treatment plan.

10. The computer-implemented method of claim 1, wherein the action policy is generated for a specific clinical scenario.

11. The computer-implemented method of claim 1, further comprising, prior to performing the evaluation of the first treatment plan, generating an entry in the action policy based on a first reward value that is associated with the action.

12. The computer-implemented method of claim 11, wherein the action is associated with meeting a threshold condition of the dose-volume objective included in the set of one or more dose-volume objectives and the first reward value is greater than a second reward value that is associated with an action that exceeds the threshold condition.

13. A non-transitory computer readable medium storing instructions that, when executed by a processor, cause the processor to perform the steps of:
performing an evaluation of a first treatment plan for the target volume by comparing a dose-volume distribution based on the first treatment plan to a dose-volume objective included in a set of one or more dose-volume objectives;
based on the evaluation and on an action policy that indicates multiple actions for improving the treatment plan, selecting from the multiple actions an action that modifies at least one dose-volume objective parameter for the dose-volume objective included in the set of one or more dose-volume objectives;
generating a modified dose-volume objective by performing the action on the dose-volume objective included in the set of one or more dose-volume objectives; and
causing an optimization application to generate a second treatment plan that meets the modified dose-volume objective.

14. The non-transitory computer readable medium of claim 13, wherein the at least one dose-volume objective parameter comprises at least one of a minimum dose distribution within the target volume, a maximum dose distribution within an organ at risk that is proximate the target volume, or a factor included in a cost function that quantifies a penalty for a treatment plan failing to achieve the dose-volume objective.

15. The non-transitory computer readable medium of claim 13, wherein selecting the action comprises selecting at least one action from an action space that includes changing a threshold value associated with the at least one dose-volume objective included in the set of one or more dose-volume objectives; repositioning, on a dose-volume histogram, a dose-volume curve associated with the at least one dose-volume objective included in the set of one or more dose-volume objectives; and modifying a weighting factor associated with the at least one dose-volume objective included in the set of one or more dose-volume objectives.

16. The non-transitory computer readable medium of claim 13, further comprising instructions that, when executed by the processor, cause the processor to perform the step of:
prior to causing the optimization application to generate the second treatment plan, generating a modified treatment plan by modifying the first treatment plan with the modified dose-volume objective parameter.

17. The non-transitory computer readable medium of claim 16, wherein causing the optimization application to generate the second treatment plan comprises causing the optimization application to perform at least one iteration of an optimization process on the modified treatment plan.

18. The computer-implemented method of claim 1, wherein a trained artificial intelligence agent selects the action from the multiple actions.

19. The computer-implemented method of claim 18, wherein the trained artificial intelligence agent learns the action policy via training to maximize a reward function to improve a treatment plan for delivering radiation treatment to the target volume.

20. The computer-implemented method of claim 19, wherein the reward function is based on the set of one or more dose-volume objectives.

* * * * *